United States Patent [19]

Harris

[11] 4,331,603

[45] May 25, 1982

[54] PROCESS FOR IMPROVING THE FRAGRANCE PROPERTIES OF MACROCYCLIC COMPOUNDS OBTAINED BY THERMAL DEPOLYMERIZATION

[75] Inventor: Eugene G. Harris, West Chester, Ohio

[73] Assignee: Emery Industries, Inc., Cincinnati, Ohio

[21] Appl. No.: 171,554

[22] Filed: Jul. 23, 1980

Related U.S. Application Data

[63] Continuation-in-part of Ser. No. 43,392, May 25, 1979, abandoned.

[51] Int. Cl.$^3$ ............... C07D 321/12; C07D 321/00; C07D 323/00; C07D 309/30
[52] U.S. Cl. .................................. 549/228; 549/266; 549/267; 549/271
[58] Field of Search .................. 260/340.2, 343, 343.5

*Primary Examiner*—Norma S. Milestone
*Attorney, Agent, or Firm*—Kenneth D. Tremain

[57] ABSTRACT

A process is provided whereby the malodorous and undesirable constituents present with macrocyclic fragrance compounds obtained by the thermal depolymerization of polyesters are removed. The process involves contacting the macrocyclic compound maintained in a liquid state with ozone or ozone and an aqueous solution of hydrogen peroxide.

15 Claims, No Drawings

PROCESS FOR IMPROVING THE FRAGRANCE PROPERTIES OF MACROCYCLIC COMPOUNDS OBTAINED BY THERMAL DEPOLYMERIZATION

CROSS REFERENCES TO RELATED APPLICATIONS

This is a continuation-in-part of my copending application Ser. No. 043,392, filed May 25, 1979, now abandoned.

BACKGROUND OF THE INVENTION

Macrocyclic compounds having olfactory properties similar to the natural musks and processes for their preparation are known. The process most commonly used and presently considered to be the only acceptable method for the commercial preparation of these macrocyclic compounds is the depolymerization of linear polyesters accompanied by ring closure to form the macrocycle.

U.S. Pat. No. 2,092,031 discloses a process for the preparation of cyclic esters having more than seven atoms in the ring via depolymerization of the corresponding linear polyester by heating the polyester under vacuum in the presence of a metal catalyst. Similar processes have also been described in British Pat. No. 1,108,720, U.S. Pat. No. 3,431,279, Czech Pat. No. 108,762 and by E. W. Spanagel et al. in *J. Am. Chem. Soc.*, 57, 929,934 (1935).

While these thermal depolymerization processes are extremely useful, there are certain problems associated with their use. Most of these problems are the result of the highly viscous reaction mass and the difficulty in achieving good heat transfer within such a mass. Even when operating the process as a batch-type operation with a relatively small unit charge or when operating in a continuous or semi-continuous manner with efficient agitation, such as described in U.S. Pat. No. 4,165,321, some thermal decomposition will result. The thermal decomposition products not only discolor the resulting product but also impart a characteristic "amber" odor. The nature of these malodorous bodies is not known, however, their presence in the finished product is objectionable to perfumers even when present in trace amounts which are not easily detected or identified with sophisticated instrumentation or by analysis. The malodorous constituents cannot be completely removed by distillation and treatment with charcoal, activated carbon or clays, while significantly improving the color of the product, will not completely eliminate these undesirable odor bodies.

It would be highly desirable if a process were available for the removal of such malodorous components which detract from or mask the desired olfactory properties of the macrocyclic fragrance compound. It would be even more advantageous if such a process were adaptable to commercial operation and, in addition to enhancing the olfactory properties, if other benefits such as improving the color, thermal stability, etc. of the finished product could be obtained.

SUMMARY OF THE INVENTION

It has now quite unexpectedly been discovered that malodorous constituents such as those obtained from the thermal depolymerization of polyesters are readily, effectively and economically removed by treating the macrocyclic fragrance product with ozone. The ozone treatment is conveniently carried out at any stage in the preparation of the macrocyclic compound after the depolymerization and cyclization. The process involves intimately contacting the macrocyclic product containing the malodorous material, maintained in a liquid or fluid state and most advantageously at a temperature between 40° C. and 90° C., with ozone. An amount of ozone as low as 0.001 mole per pound of product to be treated can be used but, more usually, at least 0.01 mole ozone per pound is employed.

In another aspect of the invention, ozone treatment is employed in conjunction with hydrogen peroxide treatment. These treatments may be conducted simultaneously or, as is more usually the case, carried out in separate operations in the processing of the macrocyclic fragrance compound. Where separate operations are involved the peroxide treatment may precede or follow contacting with ozone. For the peroxide treatment an aqueous solution generally containing from 15% to 50% hydrogen peroxide is intimately contacted with the macrocyclic product at a temperature from about 25° C. to about 105° C. Typically, about 0.001 to 1 mole hydrogen peroxide is used per pound of product being treated.

In a preferred embodiment of this invention, the crude macrocyclic product is contacted with ozone and distilled under reduced pressure, the distillate treated with aqueous hydrogen peroxide and subsequently treated to remove volatile components.

DETAILED DESCRIPTION

The process of this invention involves the ozone or ozone/peroxide treatment of macrocyclic compounds such as are obtained by the depolymerization of polyesters. Such depolymerization and cyclization processes are known to the art and play no part in the present invention and are typically carried out at elevated temperatures under reduced pressure in the presence of a metal catalyst. By way of illustration, typical procedures of this type are described in U.S. Pat. Nos. 2,092,031 and 4,165,321. Such depolymerizations accompanied by cyclization are usually conducted at a temperature in the range 200° C. to 400° C. and, more preferably, from 250° C. to 350° C. at a pressure below 50 mm Hg. Metal catalysts such as the oxides, hydroxides, halides or carboxylates of magnesium, titanium, manganese, iron, aluminum, cobalt, tin and lead are usually employed. The particular depolymerization method used to obtain the macrocyclic compounds is of no consequence, since due to the nature of the reaction some undesirable malodorous thermal decomposition products will result in even the most efficient process, and the resulting product can benefit from the present ozone treatment. It will be understood, however, that some products will require and benefit from the process of this invention more than others depending on the heat history and other process conditions involved in the depolymerization and macrocycle formation.

A variety of macrocyclic compounds, including cyclic esters, cyclic ether-esters, lactones and ether-lactones can be obtained by thermal depolymerization of the corresponding linear polyesters and are beneficially treated in accordance with this process. These macrocyclic compounds can have from 8 to 20 atoms in the ring but more usually will have 11 to 18 members in the ring since compounds with ring structures of this size have very desirable musk-like odors and are useful as fine fragrance chemicals for perfumes, perfume oils, perfume fixatives, colognes, aftershave lotions and the like. In these and in other related applications such as in the formulation of personal care products including bath oils, shampoos, hair rinses, deodorants, shaving creams, bar and specialty beauty soaps, etc. the presence of any malodorous constituents with the macrocyclic fragrance compound is undesirable and can not be tolerated.

More specifically the macrocyclic compounds treated in accordance with the present process will correspond to the general formulae

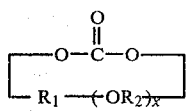 (a)

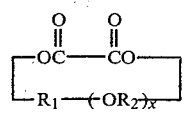 (b)

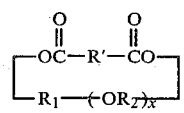 (c)

wherein R' is a bivalent hydrocarbon radical, which can be branched or straight chain, saturated or contain unsaturation, having 1 to 15 carbon atoms, $R_1$ is a saturated bivalent hydrocarbon radical having 1 to 17 carbon atoms, $R_2$ is a saturated bivalent hydrocarbon radical having 1 to 8 carbon atoms, and x is an integer from 0 to 4, and

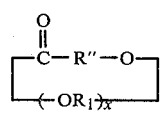 (d)

where R" is a bivalent hydrocarbon radical, branched or straight chain, saturated or unsaturated and having 1 to 18 carbon atoms, and $R_1$ and x are the same as defined above. Macrocyclic compounds corresponding to the above formulae and have especially desirable olfactory properties, and for which the ozone or ozone/peroxide treatment is particularly beneficial, are those where R' and R" are a bivalent hydrocarbon radical of the formula $+CR_3R_4)_y$ where y is an integer from 4 to 15 and $R_3$ and $R_4$ are hydrogen or a $C_{1-4}$ alkyl group; and $R_1$ and $R_2$ are saturated bivalent hydrocarbon radicals having 2 to 6 carbon atoms, and more particularly the radical —$CH_2CH_2$—.

Illustrative macrocyclic compounds of the above types obtained by thermal depolymerization include: tetradecamethylene carbonate, dodecamethylene oxalate, 7-oxa-tridecamethylene oxalate, 3,6,9-tridecamethylene malonate, dodecamethylene malonate, decamethylene malonate, ethylene suberate, ethylene azelate, 3-oxa-pentamethylene azelate, 3-methyl-pentamethylene sebacate, ethylene undecanedioate, ethylene dodecanedioate, methylene dodecanedioate, methylene brassylate, ethylidine brassylate, ethylene brassylate, ethylene-α-methylbrassylate, ethylene-α,α-dimethylbrassylate, ethylene-α,α-ethylbrassylate, pentadecanolide, 2-oxa-pentadecanolide, hexadecanolide, 3-oxa-hexadecanolide, 10-oxa-hexadecanolide, 11-oxa-hexadecanolide, and 12-oxa-hexadecanolide.

The process of this invention for the removal of the malodorous constituents which detract from the olfactory properties of macrocyclic fragrance compounds involves treatment of any of the above-identified types of macrocyclic compounds with ozone, by itself or in conjunction with aqueous hydro peroxide. To achieve the desired result intimate contact with the ozone is necessary and the material being treated is therefore maintained in a liquid state and the ozone dispersed in this liquid medium in a manner which will achieve efficient contact between the liquid and gas phases.

The amount of ozone employed to achieve removal of the malodorous bodies will vary depending on conditions, the nature of the product being treated and whether or not the product is also treated with peroxide. In general, however, at least 0.001 mole ozone per pound of product to be treated is employed. More usually the amount of ozone is 0.01 mole/lb. or higher. While up to 10 mole/lb. or more ozone can be used, practical and economic considerations dictate that the least amount of ozone necessary to effectively remove the malodorous constituents be used. In the usual practice of this invention the amount of ozone will generally not exceed 5 mole/lb. and most usually will be in the range 0.05 to 1 mole ozone per pound of product treated.

Any of the conventional methods for generating ozone are adaptable to this process and the ozone can be obtained from pure oxygen, air or other oxygen-enriched gases. The concentration of the ozone in the gas stream will vary from about 0.1 to about 10% by weight. Most usually the ozone will constitute from 0.5 to 5 wt. % of the gas mixture. Oxygen, air, carbon dioxide and inert gases such as helium and argon can be advantageously utilized with the ozone in the process. The carrier gas should be of such a type and quality so that it does not impart any odor to the resulting treated macrocyclic product. It is generally considered advantageous to generate the ozone from pure oxygen obtained from a liquid oxygen source or the like.

As has already been indicated, to obtain intimate and efficient contact of the ozone with the macrocyclic product being treated the product is maintained in a liquid or fluid state. If the material, either in the crude state or which has been subjected to one or more purification operations, is a solid or semi-solid it is heated to a temperature above its solidification point before contacting with the ozone-containing gas. If heating is required, the temperature will generally not exceed about 120° C. Even when the product being treated is a liquid at ambient temperature, ozone treatment is preferably carried out at a temperature in the range 40° C. to 90° C. While it is not necessary, diluents (primarily hydrocarbon in nature) may be included in the process to facilitate handling and contact with ozone. Suitable diluents are those not susceptible to attack by ozone or which do not otherwise interfere with the process or impart an odor to the resulting treated product.

As will be obvious to those skilled in the art, considerable variation in the process and the amount of ozone necessary to effect removal of the malodorous constituents and obtain other improvements in the finished macrocyclic product is possible. For example, the crude product obtained directly from the depolymerization can be employed and treated with ozone in accordance with the present invention. Such crude products may be solid or semi-solid masses and generally contain large amounts of undesirable by-products which impart undesirable color and odor and will accordingly require substantial ozone treatment to obtain the desired result. However, if the crude material is distilled, stripped or otherwise treated with suitable solvents or extractants to remove the bulk of the impurities present, or if the crude product is first treated with peroxide or other materials such as charcoal, activated carbon or clay, prior to ozone treatment, the amount of ozone and treatment time required to achieve an acceptable product and remove the undesirable "amber" odor may be significantly less. It should be noted, however, that without the ozone treatment none of these above-mentioned treatments of the crude product, alone or in combination, will completely remove the malodorous constituents and yield a product with excellent olfactory properties and which is acceptable to the fragrance industry. This is completely unexpected since it is possible to achieve products having acceptable color without treatment with ozone. With the present invention, however, which utilizes ozone by itself or in combination with treatment with hydrogen peroxide macrocyclic products having both acceptable color and good fragrance qualities can be obtained.

The manner in which the ozone is contacted with the macrocyclic product will vary widely depending on the particular equipment used and concentration of ozone. The equipment used to achieve contact of the macrocyclic product containing the malodorous by-products with the ozone is not critical. Any equipment or apparatus capable of achieving reasonably efficient gas-liquid contact can be employed and many commercial systems are available for this purpose. The system can consist of an elaborate countercurrent apparatus for contacting gases with liquids, such as bubble plate systems or the like, or can be a simple agitated vessel where the ozone-containing gas is introduced through a suitable dispersion tube or ring. The only limitation is that the ozone gas mixture be sufficiently dispersed to obtain efficient contact and react with and destroy the malodorous by-products. It is also possible to introduce the ozone into the system adsorbed on an inert support material such as silica gel or alumina.

By the process of this invention it is possible to enhance the fragrance qualities of macrocyclic products obtained by thermal depolymerization by treatment with ozone only. Additional advantages may be realized, however, if the ozone treatment is employed in conjunction with a peroxide treatment. Contacting with peroxide and ozone may be carried out in the same operation or they may be conducted as separate and distinct operations. Whereas contact with ozone will most generally be accomplished prior to peroxide treatment, it is possible to first contact with peroxide and then with ozone. In this latter situation, ozone may be introduced in the presence of the water introduced with the hydrogen peroxide or after all or a portion of this water has been removed.

For the process of this invention hydrogen peroxide is typically employed in view of its ready availability, ease of handling and favorable economics. Other peroxides or hydroperoxides compatible with the system may be used however. The hydrogen peroxide is usually employed as a 15% to 50% aqueous solution. Solutions having lower peroxide contents can be employed, however, the amount of water necessary to achieve the desired peroxide concentration is generally considered to be excessive. Solutions with peroxide contents above 50% may also be used but can present handling problems. It is most usual therefore to employ the readily available technical grades of hydrogen peroxide containing 25% to 50% $H_2O_2$. An amount of aqueous hydrogen peroxide is employed such that about 0.001 to 1 mole hydrogen peroxide, and more preferably 0.01 to 0.3 mole $H_2O_2$, is present per pound of product being treated.

Intimate contact of the peroxide and macrocyclic product is achieved by vigorously agitating the mixture at a temperature from about 25° C. to 105° C., and, more usually, from about 40° C. to 98° C. Any suitable stirring means capable of achieving efficient agitation of viscous masses may be used for this purpose. Contact times are governed by the efficiency of agitation, concentration of peroxide and the amount of impurities present in the product. Excessive contact times are not necessary or desirable and in most instances the contact time will be between ½ hour and 2 hours. Water introduced with the hydrogen peroxide is necessarily removed from the macrocyclic product by distilling or stripping under reduced pressure at some subsequent stage in the operation to obtain the final useful fragrance material.

For the present process and to obtain products having especially desirable fragrance qualities it is particularly advantageous if, after treatment with ozone, the macrocyclic product is subjected to distillation under reduced pressure. It is even more advantageous if the crude macrocyclic fragrance compound is first treated with ozone, vacuum distilled, and then treated with aqueous hydrogen peroxide. In the situation where peroxide treatment follows the distillation, the product is subjected to a degassing/stripping operation to remove water and other volatile materials which may be present in the product. This is conveniently accomplished by simply pulling a vacuum on the material for an extended period of time, preferably while maintaining the material at an elevated temperature but below the decomposition temperature. The stripping/degassing operation may be facilitated by passing an inert gas through the product. The inert gas is introduced subsurfacely and dispersed by means of a dispersing tube, agitation or similar means.

The following examples illustrate the ozone treatment process of the present invention more fully. For these examples all parts and percentages are on a weight basis unless otherwise indicated. Color was determined photometrically in accordance with A.O.C.S. Method Td 2a-64 and is reported as 100X the absorbance at 440 m$\mu$ and 550 m$\mu$.

EXAMPLE I

Preparation of Poly(ethylene brassylate)—A top-agitated resin kettle fitted with a distillation head and condenser was charged with 109 parts dimethyl brassylate containing approximately 2.3 mole percent methyl esters of monocarboxylic acids and 30.5 parts polymer grade ethylene glycol. A supported titanium catalyst (0.08 part), obtained by reacting tetraisopropyl titanate with a naturally acidic montmorillonite clay in accordance with the process of U.S. Pat. No. 4,032,550, was added to the reaction mixture under a positive pressure of nitrogen and heating begun. When the temperature of the reaction mixture reached about 180° C. methanol began distilling from the reaction mixture and was collected. After most of the methanol was removed and the temperature increased to about 192° C.–205° C., a vacuum of 2 in. Hg was applied and increased slowly to 30 in. Hg. Samples were periodically removed from the reaction mixture for analysis and after about 11 hours the reaction mixture had an acid value of 0.1 and hydroxyl value of 15.3. The reaction was terminated at this point and the high molecular weight poly(ethylene brassylate), viscosity 177 centistokes at 210° C., filtered to remove the supported titanium catalyst.

Depolymerization of Poly(ethylene brassylate)—Lead stearate (1.35 wt. %) was dissolved in the poly(ethylene brassylate) which was then charged into a heated two gallon stainless steel inverted vertical cone reactor fitted with two conical, helicoidal blades whose axes coincide with the cone axes of the bowl and which intermesh as they rotate ($\sim$20 rpm) in opposite directions to provide top-to-bottom mixing throughout the total volume of the reaction mixture. The blades were positioned within the reactor so that the maximum blade-to-wall clearance was about 0.25". A vacuum of about 1–2 mm Hg was maintained and poly(ethylene brassylate) metered into the reactor at a rate of approximately four pounds per hour for the first two hours, after which time the rate adjusted to 1.5 pounds per hour and the addition continued for another 4½ hours. Crude ethylene brassylate was continuously distilled from the reactor and collected. The rate of ethylene brassylate recovery was essentially constant after about 1½ hours and was maintained for about 12 hours after which time it slowly decreased as the amount of poly(ethylene brassylate) in the reactor was depleted. When the rate of ethylene brassylate recovery dropped below 0.25 pound per hour, heating was discontinued and the reaction terminated.

Ozone Treatment of Ethylene Brassylate—The resulting crude ethylene brassylate (color 54/94) was charged to a mixing vessel equipped with a high-speed motor-driven stirrer and heated at 65° C.–76° C. with vigorous agitation while introducing an oxygen-ozone mixture (5.9% $O_3$) subsurfacely through a sparge ring. The $O_2/O_3$ gas mixture was introduced at a 3 SCFM and essentially all the ozone was being utilized. After 6 hours the color of the product was significantly improved (93/100) and ozone treatment was terminated. A total of 0.084 mole ozone per pound was utilized in the treatment and, in addition to the improvement in the color of the product, the fragrance of the material was markedly enhanced.

The product was even further improved by distilling under reduced pressure (2–3 mm Hg) over the temperature range (pot) 171°–218° C. After removal of a fore cut (5% of the total product being distilled), the main cut (78%) was collected in the temperature range 160° C. to 170° C. (vapor). The ethylene brassylate main cut (color 99/100) had an extremely pleasant musk odor with no trace of undesirable "amber" constituents.

EXAMPLE II

To demonstrate the versatility of the process of this invention and the ability to vary the length of treatment, the following experiments were conducted. Crude ethylene brassylate (480 parts) obtained by thermal depolymerization and having a color of 48/85 was treated with ozone for 8 hours at 65°–76° C. The $O_2/O_3$ mixture and rate was the same as employed for the treatment of Example I. The fragrance properties of the resulting ozone-treated ethylene brassylate product were significantly enhanced and the color was also improved (88/100). Highly refined ethylene brassylate (color 99/100) suitable for even the most critical fragrance applications was obtained upon vacuum distillation of the ozone treated product. The treatment was repeated using 496 parts crude ethylene brassylate except that the contact time was reduced to 4 hours at 70°–80° C. After treatment and distillation, the finished product had a color of 98/100 and there were no detectable off-odors.

EXAMPLE III

Ozone treatment of crude ethylene brassylate obtained from the depolymerization of poly(ethylene brassylate) was carried out as follows: Two hundred pounds of the crude product was charged to a still and maintained at 100° C. while an oxygen-ozone (4.3% ozone) mixture was introduced below the surface by means of a gas dispersion ring at a rate of 0.5 SCFM. The treatment was continued for 3 hours. At least 90% of the ozone introduced was consumed during the first hour of treatment but as the treatment continued, ozone consumption became significantly less so that at the end of the treatment period only about 20% of the ozone was being consumed. Distillation of the ozone-treated material at reduced pressure yielded a highly useful main cut (73%) of ethylene brassylate (color 97/100) which had a very pleasing musk odor. A test panel was unable to detect any undesirable "amber" odor or any other malodorous constituents which would detract from the olfactory properties of the synthetic macrocyclic musk.

EXAMPLE IV

Following the procedure of Example I a polyester was obtained from the dimethyl esters of mixed $C_7$–$C_{10}$ aliphatic dicarboxylic acids. The polyester was then depolymerized in a manner similar to that described to obtain the crude macrocyclic product (a mixture of ethylene esters of $C_7$–$C_{10}$ acids). After stripping under reduced pressure the product (color 59/98) was contacted with ozone (0.27 mole/lb) at about 65° C. with vigorous agitation.

After the treatment period (5 hrs), both the odor and color (86/99) of the product, were significantly improved. Subsequent distillation of the ozone-treated product gave further color improvement (98/100) and a highly useful fragrance composition with no detectable malodorous constituents.

EXAMPLE V

To further demonstrate the versatility of the present treatment method and the ability of the ozone treatment to be employed in conjunction with other agents, 500 parts crude ethylene brassylate (color 61/92) was contacted with ozone in the presence of 0.01% sodium borohydride. The temperature was maintained at 100° C. during the 1.5 hour treatment period. The color of the crude product was significantly improved by such treatment to 95/100 and with distillation was further improved to 100/100. Also the olfactory properties of both these products were enhanced by the elimination of undesirable odor bodies.

For the purpose of comparison and to demonstrate the need for treatment with ozone, 500 parts of crude ethylene brassylate (color 45/92) was combined with 0.2% sodium borohydride and heated at 90°–100° C. with stirring for 1.5 hours. While the color of the treated product was slightly improved (47/94) there was no significant improvement in the fragrance properties and the undesirable odor constituents were still present. Even upon distillation, the undesirable odor bodies could not be eliminated although the color was further improved.

When the crude material employed in the above experiments was treated only with ozone in accordance with the procedures described in the earlier examples, both the color and odor of the undistilled and distilled products were as good as obtained with the ozone/sodium borohydride treatment.

EXAMPLE VI

Employing a treatment procedure similar to that described in Example I a simple of crude ethylene brassylate (color 42/96) was contacted with ozone in accordance with the method of this invention. The resulting ozone-treated product was then vacuum distilled and yielded very high quality ethylene brassylate having excellent color (99/100) and musk fragrance with no trace of any off-odors.

A sample of the crude ethylene brassylate not previously treated with ozone was vacuum distilled in an identical manner. The color of the resulting ethylene brassylate was only 85/96 and the product had a very poor and unacceptable odor. By treatment of this latter product containing the undesirable malodorous constituents with a small amount of ozone at 70°–80° C. and degassing, the color and odor qualities of the product were markedly improved and were comparable to that obtained when the crude ethylene brassylate was first ozonized and then distilled.

EXAMPLE VII

Air-oxidized pentadecanolide, color 75/94 and having undesirable odor, was treated in accordance with the process of this invention to improve the color and odor properties of the product. Eighty-eight parts of the pentadecanolide was treated with ozone (0.68 mole/lb. pentadecanolide) at 50°–60° C. The material was then vacuum distilled using a short-path still at 141°–146° C. and 1.6 mm Hg. The main cut obtained from this distillation, after a 12–15% fore cut had been removed, had a color of 98/100 and had excellent odor qualities. All of the malodorous constituents present in the initial air-oxidized pentadecanolide sample were effectively removed by this treatment.

When a sample of the original air-oxidized pentadecanolide was short-path distilled in the same manner, and after removal of 12–15% forecut, the resulting product (color 97/100) had unacceptable olfactory properties. The undesirable odor constituents present in the initial sample were still evident and masked the desirable musk fragrance of the pentadecanolide.

EXAMPLE VIII

The unexpected nature of this invention is further evident from the following experiment wherein distilled ethylene brassylate having a color of 85/97 and having a marked "amber" odor was treated with a bleaching charcoal. Such treatments are typically used with ester products (such as ester plasticizer and lubricant compositions) to improve the color and odor of these products. For this example, 250 parts distilled ethylene brassylate was combined with 25 parts bleaching charcoal (Darco G-60) and agitated at 80° C. for 1 hour. The product was then cooled and filtered. While there was a significant improvement in the final color (98/100) of ethylene brassylate there was no noticeable improvement in the fragrance qualities of the charcoal treated material.

EXAMPLE IX

To demonstrate the ability to employ peroxide treatment in combination with the ozone treatment, 2055 gms crude ethylene brassylate obtained from the thermal depolymerization of poly(ethylene brassylate) was charged to a 3-liter glass reaction vessel equipped with an agitator, thermometer and short-path take-off connected to a water-cooled condenser. Thirty percent aqueous hydrogen peroxide (24.74 gms) was then added and the mixture slowly heated to 105° C. over a one hour period with agitation and then maintained at this temperature for an additional 30 minutes. Water was removed from the reactor during the heating. When water evolution slowed, a vacuum (1.2 mm Hg) was applied for 30 minutes to remove the final traces of water.

A portion (987 gms) of the product thus obtained was then contacted with ozone at 80° C. for 7 hours. The ozone was generated using a Welsbach ozone generator operating at 7 psig $O_2$ pressure, 80 volts with an oxygen flow rate of 0.04 SCFM. Ozone was introduced subsurfacely through a gas dispersion ring with vigorous agitation. Upon completion of the treatment with ozone, the product was distilled at a pressure of 0.5 to 1.2 mm Hg and, after removing a 5.1% forecut, the main cut (77.9%) was collected. The final ethylene brassylate product (color of 96/99) had an extremely pleasant musk fragrance with no trace of any undesirable "amber" odor.

Comparable results are obtained when treatment with ozone is commenced without complete removal of water introduced during the peroxide treatment.

EXAMPLE X

Utilizing a procedure similar to that described in Example IX, crude ethylene brassylate obtained by the thermal depolymerization of poly (ethylene brassylate) was contacted with ozone and peroxide to obtain a highly useful fragrance material. For this example, however, the order of treatment was reversed, i.e. the product was first treated with ozone and in a subsequent operation contacted with hydrogen peroxide. To further illustrate the versatility of the process and the ability to obtain useful fragrance quality products by a variety of methods, in one experiment (A) the product obtained after ozone treatment was directly contacted with hydrogen peroxide and then subsequently distilled and in a second experiment (B) the product was distilled after contacting with ozone and prior to treatment with peroxide.

For both experiment A and B, the crude ethylene brassylate (color 46/94) was contacted with ozone (generator operated at 7 psig $O_2$ pressure, 75 volts and $O_2$ flow rate of 0.04 SCFM) at 75° C. for approximately 12 hours. At the end of the contact period, the color of the product was improved to 87/98.

For Experiment A, a portion (886 gms) of the ozone treated material was combined with 10.91 gms hydrogen peroxide solution (30%) and vigorously agitated for 1½ hours at a maximum temperature of 105° C. A vacuum (1 mm Hg) was then applied for 30 minutes to remove the final traces of water and the product (color 86/98) vacuum distilled at 0.7–1.05 mm Hg. The main cut (676.9 gms; b.p. 155°–166° C.) obtained from the distillation had good color and a very pleasing musk odor.

In the second procedure (Experiment B), 346.5 gms of the ozone treated material was first vacuum distilled (0.78–1.2 mm Hg) and the main cut (b.p. 154°C.–180° C., 269.7 gms; color 95/99) contacted with 1% by weight hydrogen peroxide (35% aqueous) in the usual manner. At the conclusion of the peroxide treatment the final traces of water and other volatile materials were removed by applying a vacuum to the material which was maintained at about 100°–105° C. The resulting ethylene brassylate exhibited good fragrance qualities with no undesirable "amber" odor.

It is evident from the above examples that the fragrance and other qualities of macrocyclic compounds can be markedly enhanced by treatment with ozone or ozone/peroxide in accordance with the present invention. The examples clearly demonstrate that by such treatment it is possible not only to obtain products having excellent color but it is also possible to eliminate undesirable malodorous constituents which detract from the olfactory properties of these fragrance compounds and which are objectionable to perfumers. It is also shown that only when the macrocyclic product is treated with ozone, by itself or in conjunction with peroxide treatment, is it possible to obtain both improved color and eliminate undesirable odors. While it is possible to obtain products having acceptable color using other means, e.g. efficient vacuum distillation or treatment with sodium borohydride or other agents, such treatments do not eliminate the undesirable off-odors associated with macrocyclic properties.

It is only by the use of the process of this invention that the highly desired improvement of both color and odor is achieved. This is unexpected in view of the very strong oxidative ability of ozone and hydrogen peroxide and the fact that one would expect numerous oxidative by-products to be formed and detract from the odor qualities of the treated product. It is further unexpected in view of the fact that unless the product is treated with ozone at some stage in the recovery operation, that contacting with hydrogen peroxide alone will not effectively remove the undesirable malodorous bodies and yield a fragrance product acceptable to perfumers. For example, a crude sample of ethylene brassylate contacted with 0.5% hydrogen peroxide at 90° C. under nitrogen for 1 hour will improve the color of the product from 45/93 to 65/95, however, even upon distillation, though the color is further improved to 95/100, the olfactory properties are not completely acceptable.

Still other advantages are obtained by the present process. For example, the oxidative stability of macrocyclic compounds treated in this manner is enhanced. Ozone treated and distilled ethylene brassylate maintained at 205° C. while blowing air over the surface only shows about 5 units decrease in color over a 3 hour period whereas distilled ethylene brassylate (not treated with ozone prior to distillation) when subjected to the same oxidation conditions shows a decrease in color of 36 units. Ehtylene brassylate obtained in accordance with Example IX, i.e. treated with peroxide and ozone followed by distillation, also gave only 5 units decrease in color after three hours. A similar evaluation of a product which was treated with hydrogen peroxide only and then distilled, gave a color decrease of 26 units. All comparisons for these oxidative stability tests were made at a wavelength of 440 mμ.

I claim:

1. A process for improving the olfactory properties of macrocyclic fragrance compounds obtained by the catalytic thermal depolymerization of linear polyesters which comprises intimately contacting the macrocyclic compound maintained in a liquid state at a temperature up to 120° C. with at least 0.001 mole ozone per pound of macrocyclic compound said macrocyclic compound having 8 to 20 carbon atoms in the ring and having the formula:

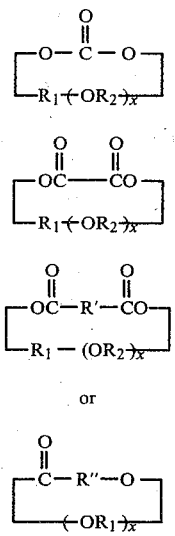

where x is an integer from 0 to 4, $R_1$ and $R_2$ are saturated bivalent hydrocarbon radicals having 2 to 6 carbon atoms, and R' and R" are bivalent hydrocarbon radicals of the formula $-(CR_3R_4)_y-$ where y is an integer from 4 to 15 and $R_3$ and $R_4$ are hydrogen or a $C_{1-4}$ alkyl group.

2. The process of claim 1 wherein the macrocyclic compound is contacted with from 0.01 to 10 mole ozone per pound at a temperature in the range 40° C. to 90° C.

3. The process of claim 2 wherein an ozone/oxygen mixture containing from 0.1% to 10% by weight ozone is employed.

4. The process of claim 1 wherein the macrocyclic compound is additionally intimately contacted with 0.001 to 1 mole hydrogen peroxide per pound of the macrocyclic compound.

5. The process of claim 4 wherein the treatment with ozone and treatment with hydrogen peroxide are carried out as separate operations in the process.

6. The process of claim 5 wherein for the ozone treatment the macrocyclic compound is contacted with 0.01 to 10 mole ozone per pound at a temperature in the range 40° C. to 90° C. and for the peroxide treatment the macrocyclic compound is contacted with 15% to 50% aqueous hydrogen peroxide at a temperature from about 25° C. to 105° C.

7. The process of claim 6 wherein for the peroxide treatment 25% to 50% aqueous hydrogen peroxide is employed and the temperature is 40° C. to 98° C.

8. The process of claim 6 wherein for the ozone treatment an ozone/oxygen mixture containing from 0.1% to 10% by weight ozone is employed.

9. The process of claim 6 wherein the macrocyclic compound is first contacted with ozone and subsequently contacted with aqueous hydrogen peroxide.

10. The process of claim 9 wherein the macrocyclic compound distilled under reduced pressure between the ozone and peroxide treatments.

11. The process of claim 10 wherein after peroxide treatment the macrocyclic compound is stripped by heating under reduced pressure at an elevated temperature to remove substantially all water and volatiles present in the macrocyclic compound.

12. The process of claim 11 wherein during the stripping operation as inert gas is passed through the macrocyclic compound.

13. The process of claims 2, 4, 5, 6, 9, 10, 11, or 12 wherein $R_1$ and $R_2$ are the radical —$CH_2CH_2$—.

14. The process of claim 13 wherein the macrocyclic compound is ethylene brassylate.

15. The process of claims 2, 4, 5, 6, 9, 10, 11 or 12, wherein the macrocyclic compound is pentadecanolide.

* * * * *

UNITED STATES PATENT AND TRADEMARK OFFICE
CERTIFICATE OF CORRECTION

PATENT NO. : 4,331,603
DATED : May 25, 1982
INVENTOR(S) : Eugene G. Harris

It is certified that error appears in the above-identified patent and that said Letters Patent are hereby corrected as shown below:

```
Column 4, line 8, "hydro" should read --- hydrogen ---.
Column 7, line 1, "192°C." should read --- 195°C. ---.
Column 9, line 14, "simple" should read --- sample ---.
Column 13, line 2, --- is --- should be inserted after "compound".
```

Signed and Sealed this

Thirty-first Day of August 1982

[SEAL]

Attest:

Attesting Officer

GERALD J. MOSSINGHOFF

Commissioner of Patents and Trademarks